United States Patent
Carnali et al.

(10) Patent No.: US 7,241,724 B2
(45) Date of Patent: *Jul. 10, 2007

(54) PERSONAL CARE COMPOSITIONS COMPRISING ALKYL PHOSPHATE SURFACTANTS AND SELECTED AUXILIARY SURFACTANTS

(75) Inventors: Joseph Oreste Carnali, Newtown, CT (US); Kavssery Parameswaran Ananthapadmanabhan, Woodbury, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/473,169

(22) Filed: Jun. 22, 2006

(65) Prior Publication Data

US 2007/0042922 A1 Feb. 22, 2007

Related U.S. Application Data

(63) Continuation-in-part of application No. 11/207,053, filed on Aug. 18, 2005, now abandoned.

(51) Int. Cl.
*C11D 3/36* (2006.01)
*C11D 1/10* (2006.01)

(52) U.S. Cl. ............... 510/130; 510/119; 510/437; 510/155; 510/222; 510/228; 510/133; 510/347; 510/423; 510/431; 510/436

(58) Field of Classification Search ............... 510/119, 510/130, 437, 155, 222, 228, 133, 347, 423, 510/431, 436
See application file for complete search history.

(56) References Cited

U.S. PATENT DOCUMENTS

| | | | | |
|---|---|---|---|---|
| 4,139,485 | A | * | 2/1979 | Imokawa et al. ........... 510/236 |
| 4,526,710 | A | * | 7/1985 | Fujisawa et al. ............ 510/159 |
| 4,758,376 | A | * | 7/1988 | Hirota et al. ................ 510/467 |
| 5,041,283 | A | * | 8/1991 | Kita et al. .................... 424/64 |
| 5,635,970 | A | | 6/1997 | Shirota et al. |
| 5,653,970 | A | * | 8/1997 | Vermeer ................... 424/70.24 |
| 6,566,408 | B1 | * | 5/2003 | Cotrell et al. ................. 516/56 |
| 2004/0136942 | A1 | * | 7/2004 | Yamazaki ................ 424/70.17 |
| 2004/0228822 | A1 | * | 11/2004 | Khaiat et al. ............ 424/70.14 |

FOREIGN PATENT DOCUMENTS

| EP | 0 449 503 A2 | 10/1991 |
|---|---|---|
| EP | 0 559 375 A1 | 9/1993 |
| EP | 1 621 603 A1 | 2/2006 |

OTHER PUBLICATIONS

Co-pending application: Camali et al., U.S. Appl. No. 11/473,167, filed Jun. 22, 2006.

* cited by examiner

*Primary Examiner*—Charles Boyer
(74) *Attorney, Agent, or Firm*—Ronald A. Koatz

(57) ABSTRACT

The invention provides personal care compositions comprising both alkyl phosphate surfactants and selected auxiliary surfactant. By using specific auxiliary surfactant whose pKa is higher than that of the alkyl phosphate surfactants, particularly in specific rations, it is possible to prepare milder compositions.

6 Claims, 2 Drawing Sheets

PERSONAL CARE COMPOSITIONS COMPRISING ALKYL PHOSPHATE SURFACTANTS AND SELECTED AUXILIARY SURFACTANTS

CROSS REFERENCE TO RELATED APPLICATIONS

The subject application is a continuation-in-part application of parent application, U.S. Ser. No. 11/207,053, filed Aug. 18, 2005, now abandoned.

FIELD OF THE INVENTION

The present invention relates to personal care compositions (e.g., bar and/or liquid) comprising phosphate surfactants (e.g., monoalkyl phosphate ester salts or MAPs) used in combination with specifically selected auxiliary surfactants. The combination of alkyl phosphates and the specifically selected surfactants particularly when used in specifically defined ratios and in defined pH range, has been found to significantly enhance mildness (measured by percent zein dissolution) of the surfactant system compared to use of alkyl phosphates alone or alkyl phosphates used in combination with different auxiliary surfactants. The compositions also have good foaming ability, even at acidic conditions.

BACKGROUND

Thousands of surfactants may be used in personal care/personal wash compositions. Among these are included sulfates, carboxylates, sulfonates etc. Formulators are constantly looking for surfactants or surfactant systems which are mild to the skin (measured for example by percent of zein dissolved by the surfactant wherein, the less zein which is solubilized, the milder is the surfactant considered).

One surfactant system which is believed to be mild relative to others is a system comprising alkyl phosphate surfactants. Typically, alkyl phosphates are commercially available as mixtures of mono- and di-alkyl esters and it is common to quote the ratio of mono to dialkyl ester, designated as MAP/DAP (monoalkyl phosphate to di-alkyl phosphate) ratio. Monoalkyl esters are diacids and possess two equivalence points, corresponding successively to the formation of the mono and di-salt with increasing degree of neutralization. Dialkyl esters are monoacids and possess a single equivalence point which corresponds approximately with the formation of the mono-salt in the monoalkyl esters.

Unexpectedly, applicants have found that, when alkyl phosphates are blended with specific weak acid auxiliary surfactants, particularly at defined ratios, the resulting systems are perceptibly more mild than the phosphate system alone. Compositions are also adequately foaming, even at the acidic pHs of the invention. Enhanced mildness is specific to conditions in which the alkyl phosphate is at least partially in the mono-salt form while the auxiliary surfactant is undissociated. In a companion application filed on same date as the subject application, applicants claim compositions where phosphate surfactant is combined with weak acid auxiliary agents (e.g., alcohols) generally.

U.S. Pat. No. 4,139,485 to Imokawa et al. discloses use of alkyl phosphate.

U.S. Pat. No. 6,566,408 to Cotrell et al. discloses compositions comprising alkyl ester salts and amphoteric surfactants.

U.S. Pat. No. 4,758,376 to Hirota et al. (Kao) discloses alkyl phosphate ester surfactants (e.g., mixture of mono- and di-alkyl phosphates) which may be used with auxiliary surfactants. The pH at which the systems are used (e.g., $\geq 7$) are high enough, however, that all surfactants (including auxiliary) are in salt form (i.e., are neutralized). While not wishing to be bound by theory, it is believed that only when the phosphate ester surfactant is neutralized but the auxiliary surfactant is not (because it is too weak an acid to deprotonate) will it be possible to form the necessary complex between MAP/DAP salt and undissociated auxiliary surfactant. When both are in salt form, the complex will not form, or at least not enough will form to significantly enhance mildness. Further, in the reference, auxiliary surfactant is used at low levels.

U.S. Pat. No. 4,526,710 to Fujiwara discloses triethanol ammonium laurate blended with dimethyl amine oxide to improve foaming of MAP/DAP mixtures. Auxiliary surfactant is used in salt form, not in an undissociated form where it can form a complex with MAP and/or DAP salts.

Other references include U.S. Publication No. 2004/0228822 to Khaiat; U.S. Publication No. 2004/0136942 to Yamazaki and U.S. Pat. No. 5,635,970 to Vermeer. In these references, ratio of alkyl phosphate to auxiliary surfactant is always outside specific ranges of claimed invention (i.e., 51:49 to 70:30, preferably 55:45 to 65:35) on upper and/or lower range.

Applicants are aware of no art disclosing the combination of alkyl phosphate ester compositions (e.g., comprising blends of mono- and di-alkyl ester salts) and specifically selected weak acid auxiliary surfactants, wherein said auxiliary surfactants are employed at conditions under which the auxiliary surfactant is undissociated (e.g., retain hydrogen and is not neutralized), the ratio of phosphate surfactant to auxiliary surfactant preferably being close to 1:1 (e.g., 55:45 to 70:30), and pH about 4.5 to 6.5.

BRIEF DESCRIPTION OF THE INVENTION

The present invention relates to personal product (liquid or bar) compositions comprising:

5-85% by wt. of a surfactant system (wherein preferably greater than 50%, more preferably 60% or greater, even more preferably 80 to 100% of the surfactant system comprises alkyl phosphate surfactant/auxiliary surfactant system noted below) wherein said surfactant system comprises a mixture of alkyl phosphate ester salt composition; and auxiliary surfactant;

wherein said auxiliary surfactant has a pKa higher (i.e., is a weaker acid) than that of the first ionizing H+ (e.g., whether on the MAP to yield a mono-salt before subsequent neutralization to the di-salt or on the DAP to yield a mono-salt without further neutralization since there is no further available hydrogen to deprotonate) on said alkyl phosphate ester salt compositions.

In a preferred embodiment of the invention the chain length of the auxiliary surfactant is substantially proximate (within +/−4, preferably +/−2 carbon chain lengths) to that of the chain length of the alkyl phosphate ester composition. If there is a chain length distribution in the alkyl phosphate ester composition, then it is preferred that the average of this distribution be proximate to that of the auxiliary surfactant. It should be noted that the alkyl chain length distribution of the MAP species will often be identical to that of the chains on the DAP species because of the way these materials are synthesized.

The molar ratio of alkyl phosphate ester to auxiliary surfactant is typically at least 1:1 and may be, for example from 51:49 to 70:30, preferably 55:45 to 70:30 or 55:45 to 65:35.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

Figure 1:
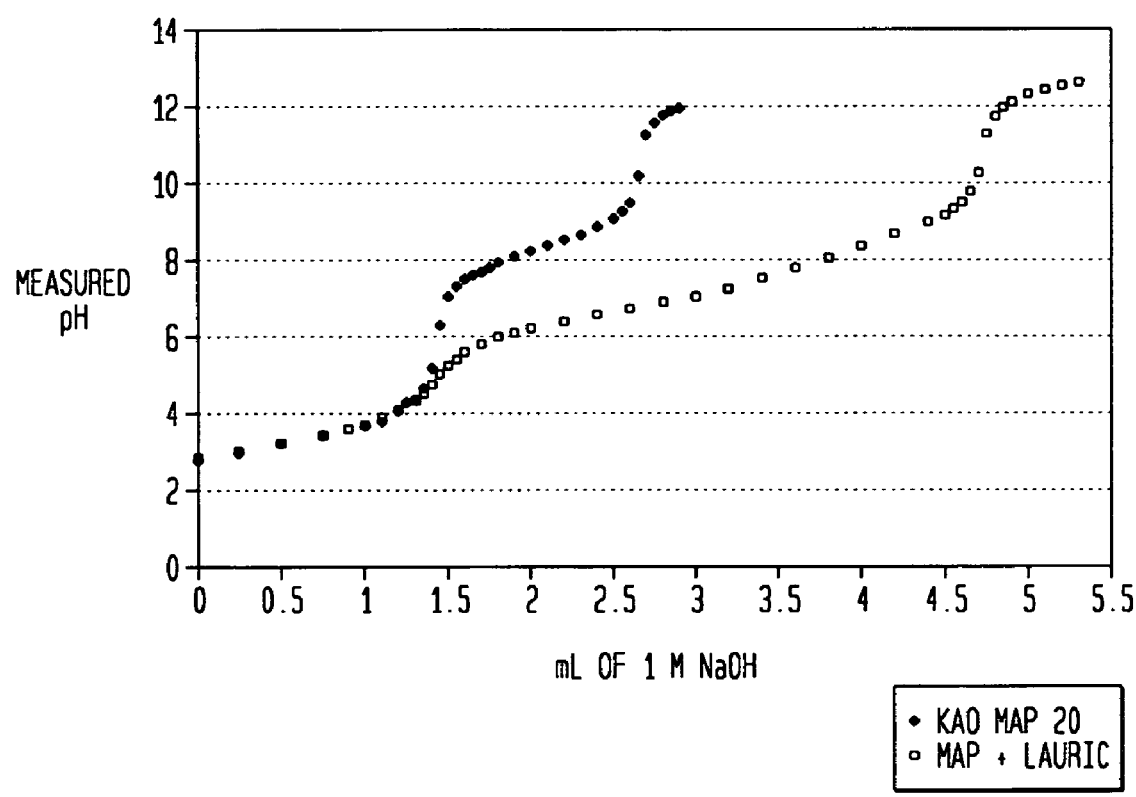
FIG. 1 is a figure showing potentiometric titration (using 1 molar NaOH base titrant) of an alkyl phosphate ester formulation (MAP 20) with and without dodecanoic acid measured in 60/40 vol/vol ethanol/water. As seen, at the initial part of titration curve, the data for MAP alone coincides with that of MAP and auxiliary surfactant. In this low pH region, because MAP is a stronger acid than lauric acid (pKa for dissociation of the first proton of the MAP head group has been estimated to be about 2 in water) it will dissociate (releasing H+ to form the mono-salt) as titrant is added, while lauric acid (dodecanoic acid), a weaker acid, will tend to stay in non-salt, unneutralized form. As additional base is added, the base begins to neutralize the second acidic proton on MAP to form the di-salt and also now begins to form a salt of the auxiliary surfactant (sodium dodecanoate). While not possible to distinguish the latter two neutralization processes, it can be concluded from the MAP/auxiliary mixtures which are disclosed that a pH region exists in which the weak acid auxiliary surfactant is essentially unneutralized (not in salt form) while the MAP is partially to essentially all in the mono-salt form. For the case of dodecanoic acid, this pH range (at which it will stay unneutralized) extends up to about pH 5.5. It is believed that as long as the auxiliary is undissociated/unneutralized (at a pH between about the pKa of the first proton of phosphate head group and the pKa of the auxiliary surfactant) one will get "complexing" between the auxiliary surfactant and the alkyl phosphate. While not wishing to be bound by theory, it is believed that the complex is less irritating to skin than are the uncomplexed species.
Figure 2:
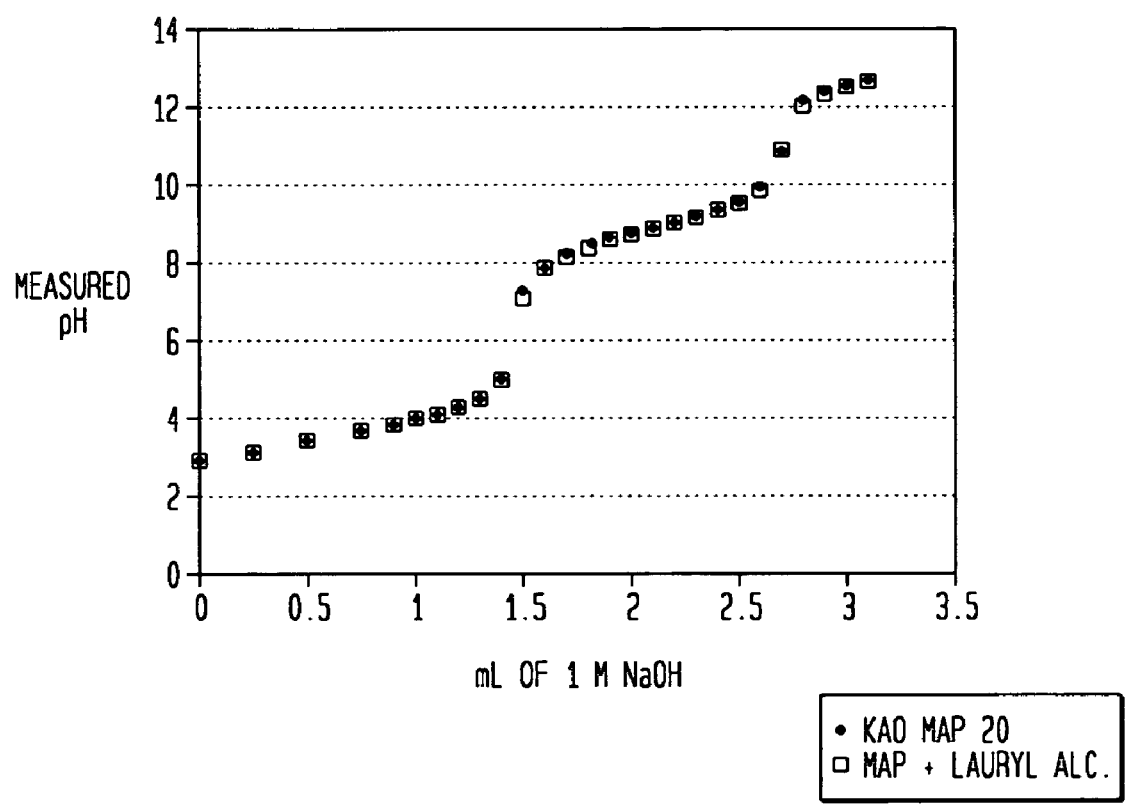
FIG. 2 is a figure showing the potentiometric titration (using 1 molar NaOH base titrant) of an alkyl phosphate ester formulation (MAP 20) with and without dodecanol measured in 60/40 vol/vol ethanol/water. For the case of dodecanol as an auxiliary agent, the pH range over which the MAP acid is largely in the mono-salt form and the auxiliary alcohol is essentially undissociated extends up until the formation of the MAP di-salt (in excess of pH 8). Thus for the case of dodecanol, we can expect complexation of MAP and an auxiliary agent (leading to less irritation by surfactant) over the pH range 3-8.

The present invention relates to personal care compositions (e.g., personal care bar or liquid compositions) comprising alkyl phosphate ester salt compositions (alkyl phosphate surfactants) used in combination with auxiliary surfactants to provide milder overall compositions. Mildness is measured by the percent of zein solubilized wherein the greater the amount of zein dissolved, the less "mild" is the surfactant. As indicated above, the differential in pKa between alkyl phosphate and auxiliary surfactant leads to the formation of a complex believed to be less irritating than the uncomplexed species.

More specifically, the compositions of the invention comprise 5 to 85% of a surfactant system (wherein preferably greater than 50% of surfactant system comprises alkyl phosphate ester surfactant/auxiliary surfactant) comprising mixture of alkyl phosphate ester salt compositions and auxiliary surfactant;
  wherein the auxiliary surfactant has a higher pKa (is a weaker acid and will tend not to dissociate to form salt as easily) than the first ionizing H+ group in said alkyl phosphate ester compositions.

While not wishing to be bound by theory, it is believed that in the pH window between when H+ will dissociate from the alkyl phosphate ester to form the salt (because it is a stronger acid) and the salt has not formed in the auxiliary surfactant (because it is a weaker acid and has not ionized), the alkyl phosphate ester salt will complex with the auxiliary surfactant. Because of this complexation, milder formulations are formed.

This mechanism essentially repeats itself from any composition comprising alkyl phosphate ester surfactant and auxiliary surfactant wherein, as noted, the pKa of auxiliary surfactant is weaker than that of the first ionizing hydrogen on the alkyl phosphate ester composition. For a given auxiliary agent which meets this criteria, pKa above that of the first pKa for MAP, there will exist a definite pH range over which we expect MAP mono-salt/undissociated auxiliary complexation to occur. It is not possible to define specifically the pH where the complex forms since this region is defined by which auxiliary surfactant is used (i.e., by the pKa of the surfactant).

In a preferred embodiment of the invention, the chain length distribution (e.g., on the main carbon chain of the surfactant) of the auxiliary surfactant is substantially the same (with ±4, preferably ±2 carbon chain units) as the chain length distribution of the alkyl phosphate ester composition.

In another embodiment, the molar ratio of alkyl phosphate ester to auxiliary surfactant is in the range of about 51:49 to 70:30, preferably 55:45 to 70:30 or preferably 55:45 to 65:35. Lower ratios of alkyl phosphate to auxiliary agent (below 50:50) are not preferred as inadequacies will arise in the areas of foam quality and quantity.

Surfactant System

As indicated, the personal product compositions of the invention, bar or liquid, are typically comprised by 5 to 85% of the surfactant system. The exact compounds will vary depending on type of composition with liquid compositions typically comprising 10% to 75% by wt. surfactant system and bar compositions typically comprising 20 to 85% surfactants.

Other than the fact that the alkyl phosphate ester surfactant/auxiliary surfactant together preferably will comprise greater than 40%, preferably greater than 50% (up to 100%) of the surfactant system, there is no real limitation as to which other surfactants, if any, will constitute the remainder of the surfactant system. That is, the other surfactants, if any, may comprise anionic, nonionic, amphoteric/zwitterionic and/or cationic surfactant and/or mixtures of any of these. These are the same surfactants as may comprise the auxiliary surfactant except they may have lower pKa since they need not complex.

Stated differently, because different surfactants may have different pKa values, it is possible for some surfactants to be forming a complex with the phosphate surfactant (e.g., because the pH is low enough for the surfactant to still not have ionized; these are the surfactants we refer to generally as the auxiliary surfactants), while other surfactant (e.g., typically with lower pKa than the first) have ionized and will not complex. While there must be at least some surfactants, perhaps all, which will complex, there need not be any of the uncomplexing surfactant.

In any event, among the anionic surfactants which may be used (whether complexing or not) are included aliphatic surfactants (e.g., non-limiting examples include $C_8$ to $C_{22}$ alkane sulfonate or disulfonate, alkane sulfonate, hydroxy alkane sulfonate, alkyl glyceryl ether sulfonate); and aromatic sulfonate (e.g., alkyl benzene sulfonate).

Also included are alkyl sulfates (e.g., $C_{12}$-$C_{18}$ alkyl sulfate); alkyl ether sulfates; alkyl sulfosuccinates; alkyl and acyl taurates; alkyl and acyl sarcosinates; sulfoacetates, alkyl phosphates; phosphate esters; sulfoacetates; and acyl isethionates.

Zwitterionic surfactants can be broadly described as derivatives of aliphatic quaternary ammonium, phosphonium and sulfonium compounds in which aliphatic radicals can be straight or branched chain and wherein at least one aliphatic substituent contains about 8 to about 18 carbons and at least one contains an anionic group, e.g., carboxyl, sulfonate, sulfate, phosphate or phosphonate.

Amphoteric surfactants include at least one acid group (e.g., sulfonic). They include quaternary nitrogen and may include quaternary amido acids as acid group. They also generally include alkyl or alkenyl group of 7 to 18 carbons.

Nonionic surfactants which may be used include reaction product of compounds having a hydrophobic group and a reactive hydrogen (for example, aliphatic alcohols, acids, amides or alkyl phenols) with alkylene oxide, especially ethylene oxide either alone or with propylene oxide. Examples include alkyl phenols-ethylene oxide condensates and condensation products of aliphatic ($C_8$-$C_{18}$) primary or secondary linear or branched alcohols with ethylene oxide. They may also be sugar amides and alkylpolyglycosides.

Cationic surfactants include quaternary ammonium compounds such as, for example, alkyldimethyl ammonium halogenides.

Some examples of surfactants which may be used in surfactant systems of the invention include sodium lauryl ether sulfate, alkylpolyglucosides, sodium lauryl sulfate, caprylamidopropyl betaine and sodium cocoylisethionate. As noted, however, there is theoretically no limit as to which surfactant or surfactant systems may be used, except that at least some, possibly all, will complex.

As for the alkyl phosphate ester surfactant in the auxiliary surfactant system, the alkyl phosphate salts used in the invention are typically mixtures of mono- and di-alkyl ester (monoalkyl phosphate and dialkyl phosphate are also typically referred to as MAPs and DAPs). Typically, the salts are sold as a commercial composition and the composition will typically have a MAP/DAP ratio. Preferably, the ratio of MAP/DAP is 80/20 or higher for optional solubility and foaming. The alkyl phosphate salts preferably have an average chain length of at least 10 as a shorter average chain length can lead to poor foaming. Upper average chain length is preferably 16 as longer lengths can lead to reduced solubility.

A typical alkyl phosphate commercial composition is, for example MAP-20 from Kao Chemicals. Analysis of this sample by applicants resulted in samples found to have MAP/DAP weight ratio of 78/22 and containing 4.4% phosphoric acid. Exact ratios of MAP/DAP or phosphoric acid are not critical to the invention and should not be considered limiting in any way.

Generally, alkyl phosphate ester salts include alkyl ether phosphate ester salts (i.e., polyoxyalkylene derivatives of the alkanols from which they are typically derived) as well as non-alkoxylated derivatives. Preferred alkyl phosphate ester salts are mixtures (as noted above) of compounds having formula (1) and (2):

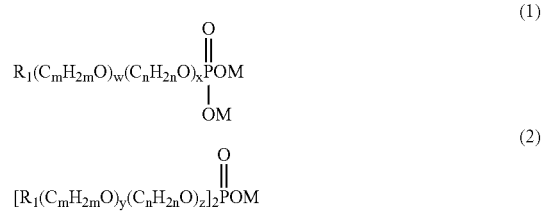

wherein $R_1$ and $R_2$ are individually $C_8$-$C_{22}$ linear or branched saturated or unsaturated hydrocarbons, m and n are individually integers from 2 to 4, w, x, y and z are individually integers from 0 to 20 and M is individually hydrogen, an alkali metal, quaternized amines, alkanolamine, or amino acid.

Auxiliary surfactants may be any surfactant having available hydrogen donating group wherein the pKa of the surfactant is higher (i.e., the surfactant is a weaker acid and will not donate hydrogen as readily) than the pKa of the first donating hydrogen on the alkyl phosphate ester surfactant.

It has been estimated that the pKa in water for the dissociation of the first proton on the alkyl phosphate ester headgroup is about 2.0 (J. Asakawa, B. A. Pethica, Journal of Colloid Interface Science, Vol. 75, No. 2, pages 441-450 (1980)).

Thus examples of auxiliary surfactants having pKa greater than this include as follows:

Classes of surfactants: alkyl carboxylates, alkyl polyether carboxylates, alkyl amino carboxylates, alkyl alcohols and ethoxylated alcohols, polyhydroxy surfactants, alkyl phenol ethoxylates—with alkyl chains linear or branched, with or without unsaturation, and free fatty acids. Specific examples of surfactants belonging to each group can be found in McCutcheons's Handbook of Industrial Detergents.

In a preferred embodiment of the invention, the chain length of the auxiliary surfactant is substantially the same length, i.e., within ±4, preferably ±2, as the average carbon chain length of the alkyl phosphate ester composition.

Also preferred is that the molar ratio of alkyl phosphate ester to auxiliary surfactant be in the range of about 51:59 to 70:30, as noted above.

The pH of the compositions of the invention is about 3.0 to 7.0, preferably 3.5 to 6.5, more preferably 4.5 to 6.5, and more preferably 4.5 to 6.0 or 4.5 to 5.75 or 4.5 to 5.5.

In another embodiment, the invention relates to a method of improving mildness of MAP blends which method comprises combining MAP blends with auxiliary surfactant which has pKa greater than that of first dissociatable proton of average MAP blend.

EXAMPLES AND PROTOCOL

The Zein Solubilization Test Procedure
1. Prepare a 5 wt. % aqueous solution of the surfactant. If the natural pH of the system differs from that desired, adjust by incremental addition of acid or base.
2. Mix 4 grams of Zein protein in 40 grams of the surfactant solution. Allow the mixture to stand at room temperature for 24 hours with frequent vigorous shaking.
3. Filter the supernatant of the Zein/surfactant mixture using a syringe filter with a 0.45 micron Nylon membrane. Dilute the filtered solution 100-fold with 2% SDS solution (i.e., 0.1 gram filtered solution diluted in 10 grams of 2% SDS solution). As a reference, also prepare a diluted surfactant solution by mixing 0.1 grams of 5 wt. % surfactant solution with 10 grams of 2% SDS solution.
4. The Zein concentration is determined using a UV/VIS spectrophotometer operated in the range 200-350 nm at a scanning rate of 800 nm/min, using a 2% SDS solution as the background. The UV absorption of the diluted surfactant solution at 278 nm is checked to make sure that the surfactant does not strongly interfere with the Zein absorption. The absorption at a wavelength of 278 nm is recorded for the diluted, filtered surfactant solution and the Zein concentration ($C_1$) determined with reference to a calibration curve of Zein solubility versus UV absorption at 278 nm. The Zein solubility in the 5 wt. % surfactant solution is C, times the dilution factor.

Mono- and Diester Content of MAPs (reference: Thomas M. Schmitt, "Analysis of Surfactants", Marcel Dekker, New York, 1992 (ISBN 0-8247-8580-0), p 44-45.

An approximate value for the mono- and diester content, as well as for any excess phosphate ion, can be obtained by potentiometric titration. An accurately weighed sample of the MAP to be analyzed is dissolved at room temperature in 65:35 ethanol/water and titrated potentiometrically with NaOH. Although the MAP acid is soluble in ethanol, precipitation will occur at the early stages of the titration in this solvent. Similarly, water is a good solvent for the fully titrated MAP, but a poor one for the MAP acid. Two inflection points will be observed for the titration, at roughly pH 5.5 and 10.0. The monoester contributes to both potentiometric breaks, as does any phosphoric acid, but the diester contributes only to the first break. Thus a second equivalence point which is less than twice the first is an indication of diester impurity. To isolate the contribution of phosphoric acid, a second titration is done on another sample of as close as possible identical weight. After the first inflection point, sufficient silver nitrate is added to precipitate all of the free phosphate ion. All soluble orthophosphates will form a characteristic yellow, silver phosphate precipitate with silver nitrate, according to $$NaH_2PO_4+3AgNO_3=Ag_3PO_4+NaNO_3+2HNO_3$$

Thus the solution pH will fall after adding the silver nitrate and a yellow precipitate will form, usually slowing the equilibration time of the pH electrode. The titration is continued until the usual second inflection point, which will be higher than that observed in the absence of silver nitrate because of the $3^{rd}$ proton from phosphoric acid which is released as $HNO_3$. Thus the difference between the second equivalence points with and without silver nitrate is the number of moles of residual phosphate. The difference between the first and second equivalencies (all without silver nitrate) equals the number of moles of monoester and phosphate—from which the monoester can be determined. Lastly, the first equivalence, minus the moles of monoester and phosphate, yields the moles of diester. With knowledge of the molecular weight of each species, the relative weight fractions can then be determined.

Example 1—Zein

To show generally the degree of harshness or non-harshness of various anionic surfactants and/or blends of surfactants used in typical personal product compositions, applicants measured and recorded the surfactants and/or blends and their Zein score as noted below.

TABLE I

Average percent Zein solubilized by a variety of anionic surfactants and blends as typically used in personal wash applications:

| Surfactant | Percent Zein solubilized |
|---|---|
| Water | 0.79 |
| Amphoacetate | 1.76 |
| Coco aminopropyl betaine (CAPB) | 3.28 |
| Sodium lauryl ether sulfate (SLES) | 4.64 |
| SLES/CAPB (2:1) | 3.23 |
| $NaC_{12}$ MAP | 4.08 |
| $KC_{12}$ MAP | 6.04 |
| TEA $C_{12}$ MAP | 4.95 |
| TEA $C_{12}$ EO MAP | 5.41 |
| TEA $C_{10-16}$ 3EO MAP | 4.49 |
| K MAP/amphoacetate (2:1) | 4.67 |
| K MAP/CAPB (2:1) | 4.21 |

All tests done at pH 6.0 with 5% total surfactant solutions. Zein and surfactant were contacted for 24 hours.

Example 2—General Effects of pH

In order to show effect of pH, applicants recorded the results of a Zein solubilization study in which the pH of the test solution is systematically varied from 6.5 to 4.5.

These are set forth in Table II below.

TABLE II

Average Zein score of TEA $C_{12}$ MAP tested over a range of pH.

| Measured pH | percent Zein solubilized |
|---|---|
| Water | 1.05 |
| 6.53 | 4.13 |
| 5.17 | 3.69 |
| 4.60 | 2.83 |

TABLE II-continued

Average Zein score of TEA $C_{12}$ MAP tested over a range of pH.

| Measured pH | percent Zein solubilized |
|---|---|
| SLES (pH 6.0) | 4.11 |
| SLES/CAPB (2:1, pH 6.0) | 3.18 |

Samples are prepared with the $C_{12}$ MAP acid and partially neutralized with triethanol amine to the indicated pH.

It will be observed that the measured Zein score falls unidirectionally with pH and falls below that of SLES/CAPB at pH 4.5. From the viewpoint of the Zein score alone, this result suggests lower pH as a means of ameliorating the harshness of MAPS. However, as noted in U.S. Pat. No. 4,139,485, formulations having a pH below 5 are generally considered as too strongly acid for skin cleansing applications.

Example 3

In order to show that specific auxiliaries could be used to enhance mildness of MAP blends if used at pH where MAPs are neutralized but auxiliaries are primarily not, applicants refer to FIG. 1.

Specifically, dodecanoic acid is one of a specific class of surfactants which is weakly acidic and specifically weaker than the first deprotonating hydrogen on the phosphate head group of MAP. The pKa in water for the dissociation of the first proton is estimated to be 2.0.

As indicated, specific neutralization of weaker and stronger acid is seen in FIG. 1.

A 50/50 weight blend of MAP 20 (a commercial $C_{12}$ MAP sample from KAO Chemicals) and dodecanoic acid (0.4 g mass of each component) was titrated potentiometically in 60/40 vol/vol ethanol/water with 1.0 M NaOH. For comparison, an identical weight of the MAP acid was titrated in the absence of dodecanoic acid. Both titration curves showed two breaks, with the first break occurring at the same level of added titrant but the second break being much delayed in the presence of dodecanoic acid. Over the initial portion of the titration curve, the data for MAP alone (diamond symbols) coincide with those for MAP plus dodecanoic acid (square symbols). Thus this portion of the titration curve corresponds to the progressive neutralization of the first acidic proton of the MAP acid. Once this neutralization is complete, additional increments in added base begin to neutralize both the second acidic proton of MAP and the dodecanoic acid, as indicated by the divergence of the two titration causes. It is not possible to distinguish these latter two processes from the titration data. It was thus concluded that, in the MAP/auxiliary agent mixtures disclosed, the weak acid auxiliary was essentially unneutralized (didn't form salt) up to a pH of 5 to 6 (preferably 5.9 and below, more preferably 5.7 and below, more preferably 5.5 and below). At levels of added base corresponding to pH's lower than about 6, MAP is partially in the mono-salt form and we speculate that it can complex with the undissociated auxiliary agent.

Examples 4-17

In one embodiment of the invention, reducing the molar ratio of alkyl phosphate ester blend to auxiliary surfactants (fatty acid) was seen to have advantages.

In this regard, applicants set forth Table III below:

TABLE III

Effect of blending $C_{12}$ MAP in varying ratio with fatty acids

| Example | Fatty Acid | % Acid | pH | Percent Zein solubilized |
|---|---|---|---|---|
| 4 | Lauric | 10 | 5.0 | 2.85 |
| 5 | Lauric | 20 | 5.0 | 2.20 |
| 6 | Lauric | 30 | 5.0 | 2.01 |
| 7 | Lauric | 40 | 5.0 | 0.12 |
| 8 | Lauric | 50 | 5.0 | 0.46 |
| 9 | Myristic | 10 | 5.0 | 2.98 |
| 10 | Myristic | 20 | 5.0 | 2.63 |
| 11 | Myristic | 30 | 5.0 | 1.76 |
| 12 | Myristic | 40 | 5.0 | 1.64 |
| 13 | Myristic | 50 | 5.0 | 1.29 |
| 14 | Capric | 20 | 5.0 | 4.23 |
| 15 | Capric | 30 | 5.0 | 2.62 |
| 16 | Capric | 40 | 5.0 | 1.46 |
| 17 | Capric | 50 | 5.0 | 0.72 |

Samples were prepared by melting $C_{12}$ MAP acid and the fatty acid at a combined 5% level in water and partially neutralized with triethanol amine to the indicated pH.

As seen, as molar range of MAP blend to auxiliary goes from 90:10 to 50:50, there is an improvement in mildness as measured by Zein solubilization.

The perhaps superior effect of lauric acid is believed due to another preferred embodiment of the invention, matching chain lengths of auxiliary carbon chain to that of average MAP blend carbon chain lengths as close as possible. Preferably chain length should be within ±4 carbons, more preferably ±2 carbons. As noted, lauric acid (average $C_{12}$ blend) matches most closely to the $C_{12}$ MAP blend.

Control and Examples 18-29

To show that blending effect works for other carboxylic acids, applicants prepared Table IV noted below.

TABLE IV

Effect of blending $C_{12}$ MAP in varying ratio with other carboxylic acids

| Example | Carboxylic Acid | % Acid | pH | Percent Zein Solubilized |
|---|---|---|---|---|
| Control | SLES | | 5.0 | 3.52 |
| 18 | Caproyl lact. | 20 | 5.0 | 3.78 |
| 19 | Caproyl lact. | 30 | 5.0 | 3.44 |
| 20 | Caproyl lact. | 40 | 5.0 | 1.07 |
| 21 | Caproyl lact. | 50 | 5.0 | 0.83 |
| 22 | Lauroyl lact. | 20 | 5.0 | 3.92 |
| 23 | Lauroyl lact. | 30 | 5.0 | 1.41 |
| 24 | Lauroyl lact. | 40 | 5.0 | 0.79 |
| 25 | Lauroyl lact. | 50 | 5.0 | 0.32 |
| 26 | Recinoleic | 20 | 5.0 | 4.56 |
| 27 | Recinoleic | 30 | 5.0 | 4.46 |
| 28 | Recinoleic | 40 | 5.0 | 4.21 |
| 29 | Recinoleic | 50 | 5.0 | 4.19 |

Specifically, Table IV describes the effect on Zein solubilization of replacing a fraction of the MAP with a non-fatty acid carboxylic acid, specifically caproyl and lauroyl lactylates, with the structure:

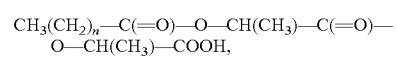

$CH_3(CH_2)_n$—C(=O)—O—CH($CH_3$)—C(=O)—O—CH($CH_3$)—COOH, where n is 8 for caproyl lactylate and 10 for lauroyl lactylate. As with the fatty acids of Table III, the influence of these non-fatty acid carboxylic acids is to dramatically reduce the Zein score. Again, the effect of the additive is greatest when the alkyl chain length matches that of the MAP. This hypothesis is supported by the results with $C_{18}$ chain ricinoleic acid, which is a fatty acid carboxylic acid with the structure

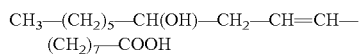

This carboxylic acid is less effective at ameliorating the apparent harshness of the $C_{12}$ MAP.

The acyl lactylates incorporated in this invention have been described in U.S. Pat. No. 5,911,981 and are commercially available from the Rita Corporation under the trade names Pationic 122A (caproyl lactylate) and Pationic 138C (lauroyl lactylate). These materials are the caproic acid and lauric acid (respectively) esters of lactyl.

Example

Control and Examples 30-38

To show effect of auxiliaries other than carboxylic acids, applicants blended $C_{12}$ MAP composition with fatty alcohol as set forth in Table V below.

TABLE V

Effect of blending $C_{12}$ MAP in varying ratio with fatty alcohols

| Example | carboxylic acid | % alcohol | pH | Percent Zein Solubilized |
|---|---|---|---|---|
| Control | SLES | | 5.0 | 3.52 |
| 30 | Decanol | 40 | 5.0 | 0.375 |
| 31 | Decanol | 50 | 5.0 | 0.24 |
| 32 | Lauryl alcohol | 10 | 5.0 | 2.69 |
| 33 | Lauryl alcohol | 20 | 5.0 | 2.19 |
| 34 | Lauryl alcohol | 30 | 5.0 | 0.8 |
| 35 | Lauryl alcohol | 40 | 5.0 | 0.33 |
| 36 | Lauryl alcohol | 50 | 5.0 | 0.05 |
| 37 | Tetradecanol | 40 | 5.0 | 1.35 |
| 38 | Tetradecanol | 50 | 5.0 | 0.69 |

Zein tests reported in Table V were all conducted at 45° C. rather than at room temperature.

Table V reports the Zein solubilization observed when a fraction of the MAP is supplemented by alkyl alcohol. As with the prior examples, the effect is quite dramatic with the Zein score falling to essentially zero for 50/50 weight ratio blends of MAP and lauryl alcohol. Further, the effects of more moderate levels of lauryl alcohol/MAP exchange are also impressive, with the Zein score falling below 1.0 already at a 70/30 MAP/alcohol ratio. Thus lauryl alcohol is a very efficient auxiliary agent at improving the mildness of MAP.

Comparing slightly longer (tetradecanol) and slightly shorter (decanol) fatty alcohols, it is seen that chain length matching to the $C_{12}$ MAP again gives the best results.

Negative Controls—Examples 39-41

To show the effect of utilizing strong acid auxiliary agents, whose pKa lies below that of C12 MAP, applicants set forth Table VI as noted below.

TABLE VI

Negative controls - $C_{12}$ MAP with strong acid auxiliary agents

| Example | Composition | pH | Percent Zein Solubilized |
|---|---|---|---|
| 39 | 50/50 $C_{12}$ MAP/SDS | 5.0 | 4.71 |
| 40 | 50/50 $C_{12}$ MAP/SLES | 5.0 | 4.00 |
| 41 | 100 SLES | 5.0 | 3.52 |

It can be observed that the strong acid auxiliary agents, whose pKa's lie at or below those of MAP, offer no reduction in the irritation potential.

Examples 42-48—Amino Acid Counterions

To show the effect of counterions other than alkali metals or alkanol amines, applicants blended $C_{12}$ MAP composition with fatty acid or fatty alcohol and amino acid counterions set forth in Table VII below.

TABLE VII

Effect of blending $C_{12}$ MAP with fatty alcohol or fatty acid using amino acid counterions

| Example | Weak Acid Auxiliary | Counterion | Percent Zein Solubilized |
|---|---|---|---|
| 42 | SLES Control | | 3.55 |
| 43 | Lauric Acid | Arginine | 0.55 |
| 44 | Lauric Acid | Lysine | 0.84 |
| 45 | Lauric Acid | Choline | 2.43 |
| 46 | SLES Control | | 3.42 |
| 47 | Lauryl Alcohol | Arginine | 1.08 |
| 48 | Lauryl Alcohol | Choline | 1.74 |

Samples were prepared by melting $C_{12}$ MAP acid in a 60/40 weight ratio with the fatty acid or the fatty alcohol at a combined 5% level in water and partially neutralized with the indicated amino acid to pH 5.

As seen, the MAP/weak acid auxiliary systems partially neutralized with the amino acid counterion gives a considerable improvement in mildness versus the SLES control as measured by Zein solubilization.

Examples 49-51—Liquid Cleansing Formulations

To further show the utility of the present invention, applicants assembled several prototype liquid compositions as follows:

| Component | | Weight Ex. 49 | Percentage Ex. 50 | % Ex. 51 |
|---|---|---|---|---|
| MAP Dodecanol | Kao MAP 20 | 11.2 | 11.2 | 11.2 |
| | | | | 7.4 |
| Dodecanoic Acid | | | 7.4 | 7.4 |
| CAPB | Cocamidopropyl betaine | | 4.5 | |
| Taurate | Sodium N-cocoyl N-methyl taurate | | | 4.5 |
| Glycerine | | 39.4 | 35.0 | 35.0 |
| TEA | Triethanol amine | 5 | 5 | 5 |
| Merquat 100 | Dimethyldiallyl ammonium chloride | 0.3 | 0.3 | 0.3 |

-continued

| Component | | Weight Ex. 49 | Percentage Ex. 50 | % Ex. 51 |
|---|---|---|---|---|
| Glydant plus | DMDM hydantoin | 0.2 | 0.2 | 0.2 |
| Water | | To 100% | To 100% | To 100% |

The first six compounds were stirred with water while heating to 70° C., then TEA was added to achieve pH 5. The Merquat polymer and Glydant Plus were added as the sample cooled. The product was a creamy paste which lathers well.

The invention claimed is:

1. A personal product composition comprising 5 to 85% by wt. of a surfactant system comprising alkyl phosphate surfactant or alkyl phosphate surfactant blends and an auxiliary surfactant selected from the group consisting of alkyl carboxylates, alkyl polyether carboxylates, alkyl amino carboxylates, polyhydroxy surfactants, alkyl phenyl alkoxylates and mixtures thereof;

wherein said auxiliary surfactant has a pKa which is higher (weaker acid) than that of average pKa of first ionizing H+ in said phosphate surfactant or alkyl phosphate surfactant blend.

wherein pH of the composition is about 4.5 to 6.5;

wherein phosphate surfactant and/or blend and auxiliary surfactant together comprise 40% or greater of the surfactant system;

wherein molar ratio of alkyl phosphate ester to auxiliary surfactant is about 55:45 to 65:35, and wherein said composition further comprises amino acid counterions.

2. A composition according to claim 1, wherein phosphate surfactant and/or blend; and auxiliary surfactant comprise 50% or greater of the surfactant system.

3. A composition according to claim 1, wherein chain length of the auxiliary surfactant is within ±4 carbons of chain length of alkyl phosphate.

4. A composition according to claim 1, wherein the molar ratio of alkyl phosphate ester to auxiliary surfactant is less than 90:10.

5. A composition according to claim 4, wherein the molar ratio is less than 80:20.

6. A composition according to claim 1, wherein pH is 4.5 to 6.

* * * * *